United States Patent

Ikebe

Patent Number: 5,329,567
Date of Patent: Jul. 12, 1994

[54] SYSTEM FOR STEREOTACTIC RADIOTHERAPY WITH A COMPUTERIZED TOMOGRAPHIC SCANNING SYSTEM

[76] Inventor: Jun Ikebe, 3-10-19 Nozawa Setagaya-ku, Tokyo 154, Japan

[21] Appl. No.: 35,037

[22] Filed: Mar. 22, 1993

[30] Foreign Application Priority Data

Mar. 24, 1992 [JP] Japan .................. 4-115116

[51] Int. Cl.5 .................................................. A61N 5/10
[52] U.S. Cl. .................................. 378/20; 378/65; 378/195
[58] Field of Search ............. 378/20, 64, 65, 68, 378/69, 195, 208, 209

[56] References Cited

U.S. PATENT DOCUMENTS

| | | | |
|---|---|---|---|
| 5,039,867 | 8/1991 | Nishihara et al. | 378/65 X |
| 5,117,829 | 6/1992 | Miller et al. | 378/65 X |
| 5,199,060 | 3/1993 | Kato | 378/195 X |
| 5,206,893 | 4/1993 | Hara | 378/68 X |

*Primary Examiner*—David P. Porta
*Attorney, Agent, or Firm*—John T. Roberts

[57] ABSTRACT

A linear accelerator having an X-ray head for emanating X-rays and a CT scanner are provided opposite to each other. The X-ray head is provided to be rotated about a horizontal axis, and such that the X-rays intersect the horizontal axis at an isocenter. A treatment couch is movably mounted on a base. After CT scanning, the treatment couch is moved onto a turntable beneath the X-ray head of the linear accelerator by the base, so that an affected part of a patient, of which position is stored in a memory at CT scanning, may coincide with the isocenter in accordance with the stored position.

6 Claims, 8 Drawing Sheets

SYSTEM FOR STEREOTACTIC RADIOTHERAPY WITH A COMPUTERIZED TOMOGRAPHIC SCANNING SYSTEM

BACKGROUND OF THE INVENTION

The present invention relates to a system for stereotactic radiotherapy using a computerized tomographic scanning system as an on-line controller, and more particularly to a system for a stereotactic radiation therapy with a linear accelerator which is operated in accordance with information obtained by the computerized tomographic scanning system.

Figure 1:
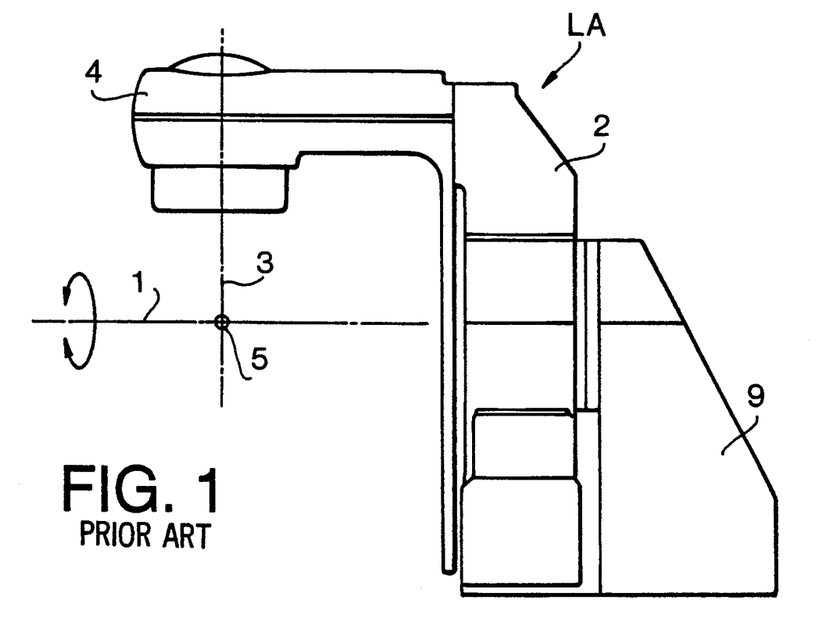
FIG. 1 shows a side view of a conventional linear accelerator.
Figure 2:
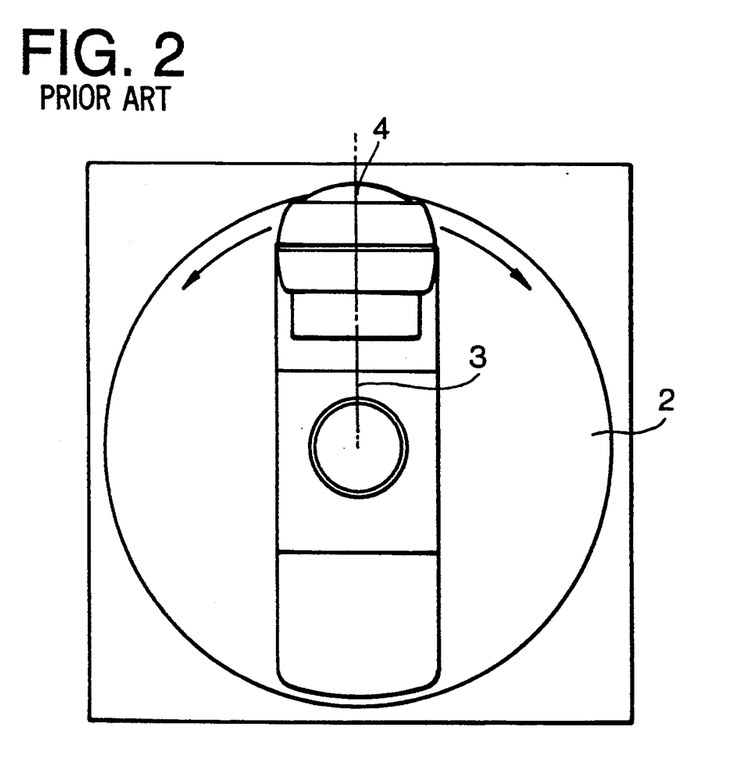
FIG. 2 is a front view of the linear accelerator.

Referring to FIGS. 1 and 2 showing a conventional linear accelerator LA, a rotating frame 2 having an X-ray head 4 is rotatably mounted on a base 9 so as to be rotated about horizontal axis 1. The X-ray head 4 is provided such that an axis 3 of X-ray beams intersects the axis 1 at an isocenter 5. Consequently, reciprocative rotation of the rotating frame 2 causes the X-rays to always pass the isocenter 5, which means that the X-rays concentrate to the isocenter 5. Therefore, an affected part of a patient is effectively treated.

However, in the conventional system, since the X-rays reciprocate in the same plane, other healthy parts in the plane may be affected by the radiation.

On the other hand, the position of the lesion is determined by the eye-measurement of the operator in accordance with CT (Computed Tomography) scan data or data obtained by MRI (Magnetic Resonance Imaging) which were obtained at another place before the treatment. Therefore, the X-rays controlled by the eye-measurement not always are irradiated to the lesion.

SUMMARY OF THE INVENTION

Accordingly, an object of the present invention is to provide a system which may exactly irradiate X-rays to an affected part.

Another object of the present invention is to minimize the dose of X-rays to other parts than the lesion.

According to the present invention, there is provided a system for stereotactic radiotherapy comprising a first apparatus having a head for emanating an ionizing radiation, the head being provided to be rotated about a horizontal axis, and such that the ionizing radiation intersects the horizontal axis at an isocenter, a second apparatus for taking a tomographic image, which is installed on the same floor as the first apparatus and has a center for the tomographic image, a base movable between the first and second apparatuses, a treatment couch horizontally movably mounted on the base, feeding means for feeding the couch with respect to the base to a longitudinal direction (Y) of the base and for feeding the couch within a vertical (X-Z) plane perpendicular to the direction (Y), positioning means for positioning the base in the second apparatus so that the positional relation between the center and the base coincides with the positional relation between the isocenter and the base, storing means for storing data on a particular position in the tomographic image, control means for controlling the feeding means so that the ionizing radiation is irradiated to a part in a patient on the couch dependent on the stored data of the position.

In an aspect of the invention, the first apparatus is a linear accelerator having an X-ray head and the second apparatus is a CT scanner.

In the system of the present invention, the CT scanner is placed opposite to the linear accelerator, and the treatment couch is used for both of the CT scanning and the radiation therapy by the linear accelerator. Immediately after the CT scanning, the treatment couch is moved onto a turntable beneath the X-ray head of the linear accelerator. The treatment is proceeded at the isocenter of the linear accelerator, while the turntable is continuously rotated about a vertical axis.

A beam of X-rays is collimated as slender as possible (about 5 mm in diameter). The beam passes through the isocenter during the continuous and reciprocative rotation of the X-ray head about a horizontal axis. On the other hand, the base and the treatment couch on the turntable is slowly rotated (half revolution per treatment) around the vertical axis passing through the isocenter. Thus, the slender X-ray beam is focused at the isocenter, whereas the path of the beam passes through the body of the patient only one time. As a result, the dose of X-rays to tissues outside the lesion can be reduced to a minimal amount. Thus, the X-ray beam forms a "radio-spot" at the isocenter.

For the treatment, the whole region of the lesion must be scanned by the radio-spot. For this purpose, the couch is moved with respect to a base thereof by servomechanisms. The servomechanisms are controlled by signals obtained by the CT scanner. To realize the production of precise CT data and exact irradiation of X-rays, matter of vital importance is to keep the lesion immobile to the treatment couch, during the time from the beginning of CT scanning to the end of treatment.

In the treatment, the center of the image plane of CT scanning must accurately correspond to the isocenter of the linear accelerator. Therefore, the mechanical alignment of the base, to the CT scanner and to the turntable of linear accelerator is ensured in the system.

The present invention is described in detail with reference to the accompanying drawings.

DETAILED DESCRIPTION OF THE PREFERRED EMBODIMENT

Figure 3:
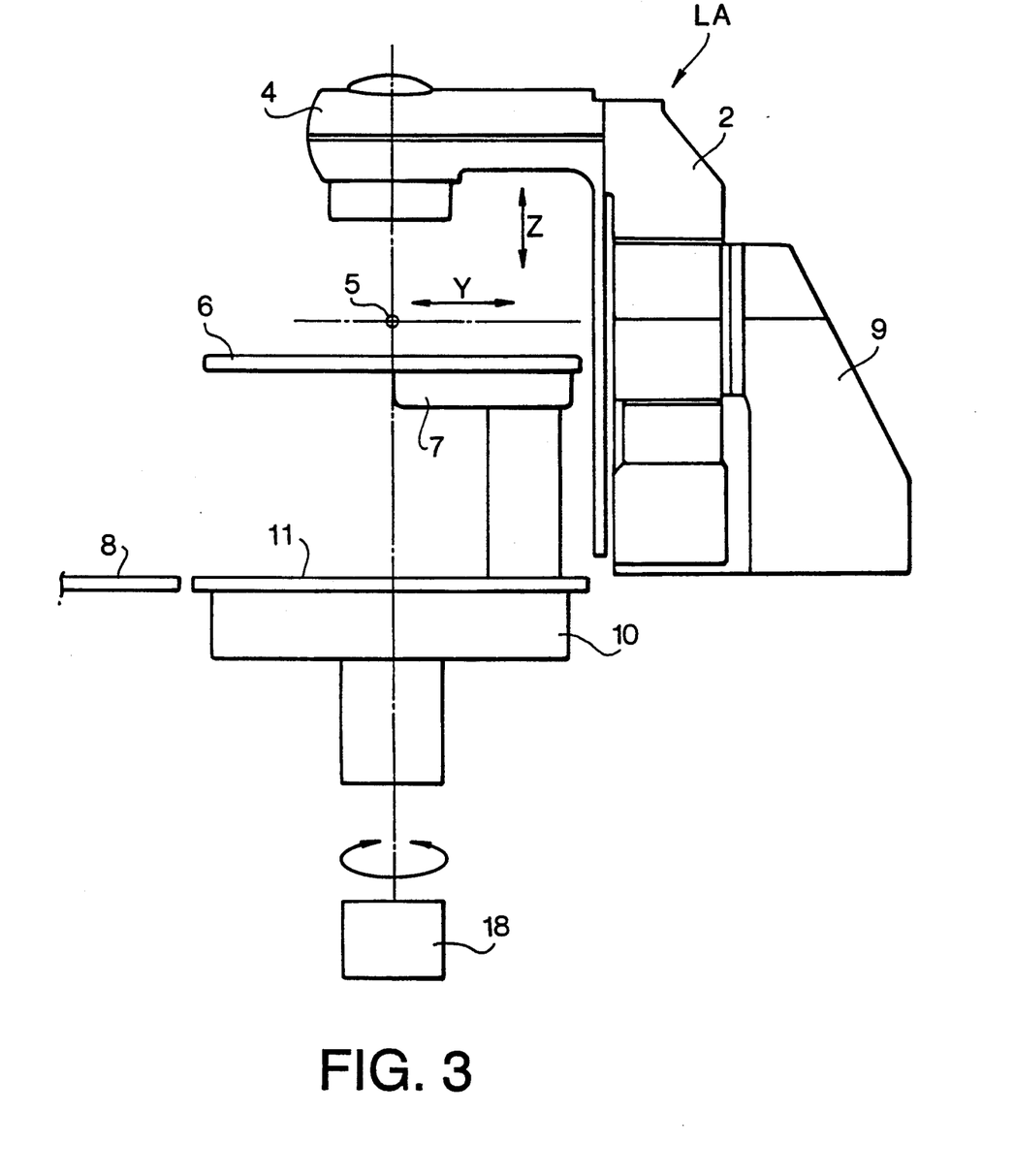
FIG. 3 is a side view of a linear accelerator used in the system of the present invention.

Referring to FIG. 3, a treatment couch 6 is mounted on a base 7. The base 7 is movably mounted on a rail 11 on a turntable 10 and clamped to the turntable. The turntable 10 is provided to be rotated about a vertical axis passing the isocenter 5. A controller 18 is provided for controlling the rotation of the turntable. The couch 6 is moved by servomechanisms equipped in the base 7 which will be described hereinafter. The Y direction of motion of the couch 6 coincides with the longitudinal axis of the base 7. The Z direction is vertical.

Figure 4:
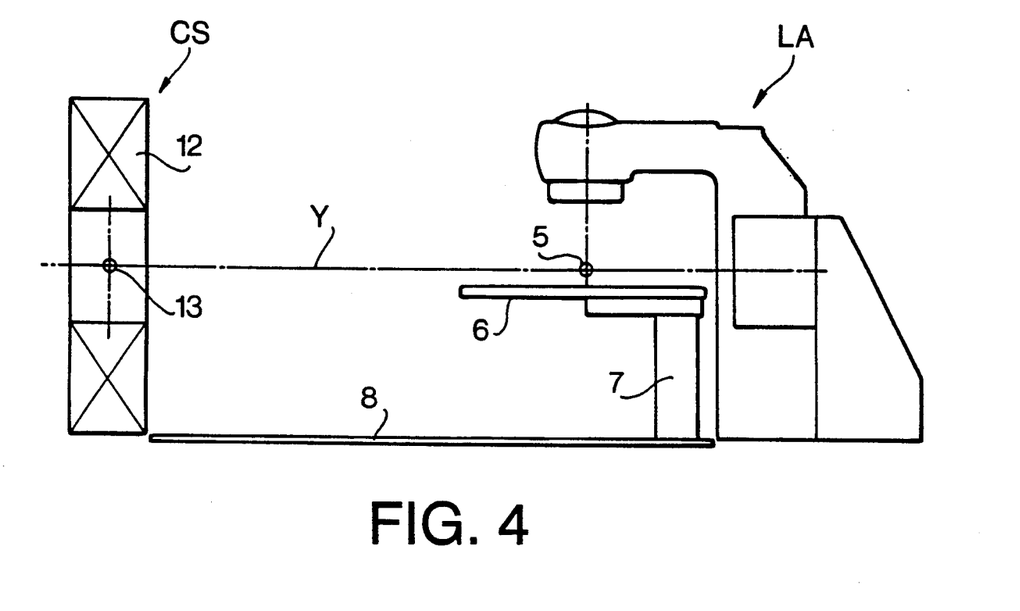
FIG. 4 is a side view of the system of the present invention.
Figure 5:
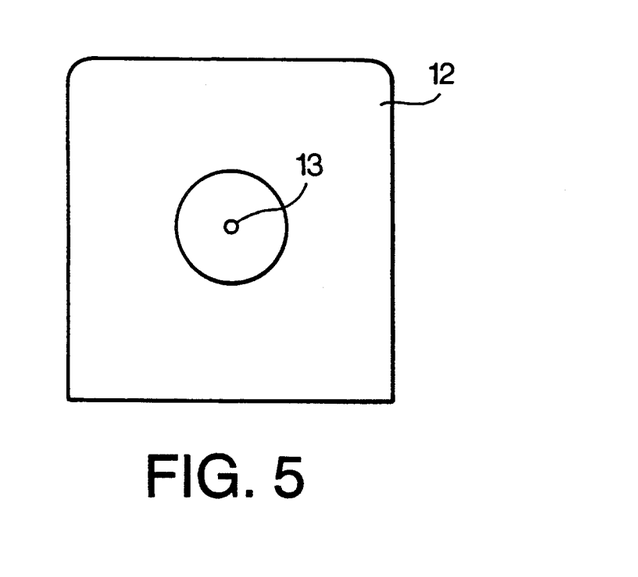
FIG. 5 is a front view of a CT scanner in FIG. 4.

Referring to FIG. 4, a CT scanner CS having a gantry 12 is provided opposite to the linear accelerator LA. A rail 8 is installed between the linear accelerator LA and the CT scanner CS. Reference numeral 13 designates a center of the CT image which is center of the CT scanner as shown in FIGS. 4 and 5. The base 7 of the couch 6 can be moved on the rail 8 to be positioned in the CT scanner CS.

The center 13 is located on the same coordinate axis Y as the isocenter 5 of the linear accelerator LA and is adapted to be marked on each image of CT slices. The center 13 serves as a virtual isocenter for the CT scanning. As described hereinafter, the mark of the center on the CT image is moved as the motion of the isocenter 5 relative to the lesion, during the irradiation with the linear accelerator.

Figure 6:
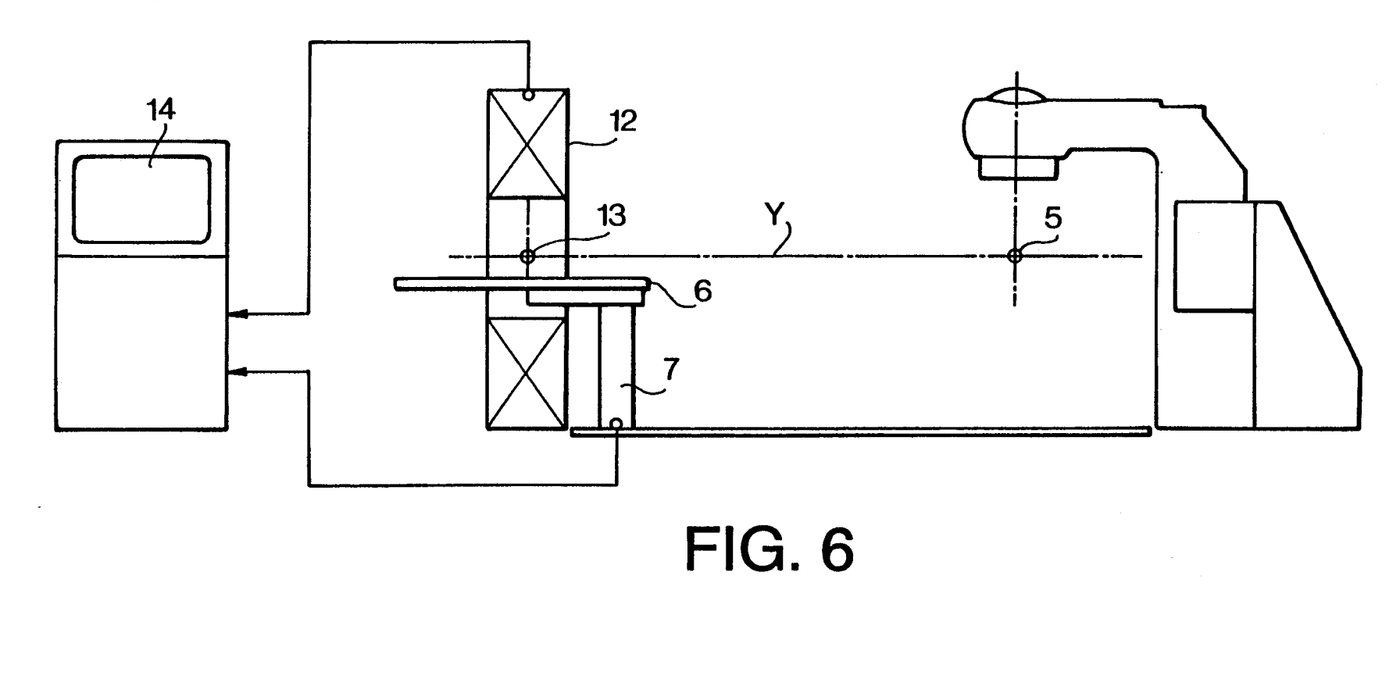
FIG. 6 is a side view of the system at CT scanning.

Referring to FIG. 6, the base 7 of the couch 6 is clamped to the gantry 12 of the CT scanner, so that the positional relation between the virtual isocenter 13 and the base 7 may exactly coincide with the positional relation between the isocenter 5 and the base 7 at the treatment by the X-rays.

Figure 7:
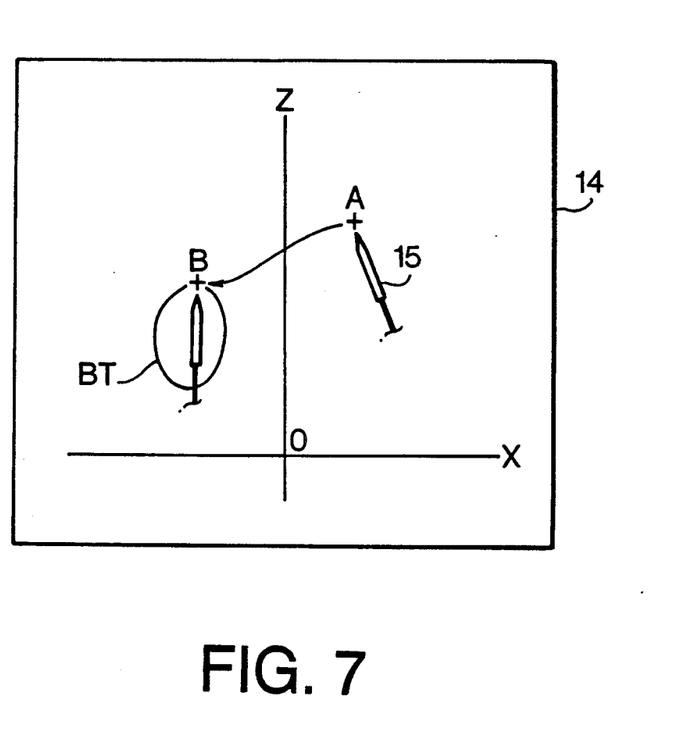
FIG. 7 shows a CRT screen.

FIG. 7 shows a CRT screen 14 in which the reference letter A designates a center position corresponding to the virtual isocenter 13 and BT shows an image of a brain tumor at one of the slices. Image data of each slice of CT scanning are read and stored in image memories like a conventional CT scanner. In addition to the image data, control data for the servomechanisms are also stored in control memories as described hereinafter.

The control data are generated on the CRT screen 14. A mark in the form of a plus at the center position A is temporarily located at the position. The plus mark can be moved from the position A to a position B in the X-Z plane by moving a tip of a light pen 15 on the screen from A to B. The increments AX and AZ of the movement of the mark from A to B are read and stored in X and Z control memories respectively. The incremental data $\Delta X$ and $\Delta Z$ are used to control the couch 6 relative to the isocenter 5 at the treatment with the linear accelerator.

Figure 8:
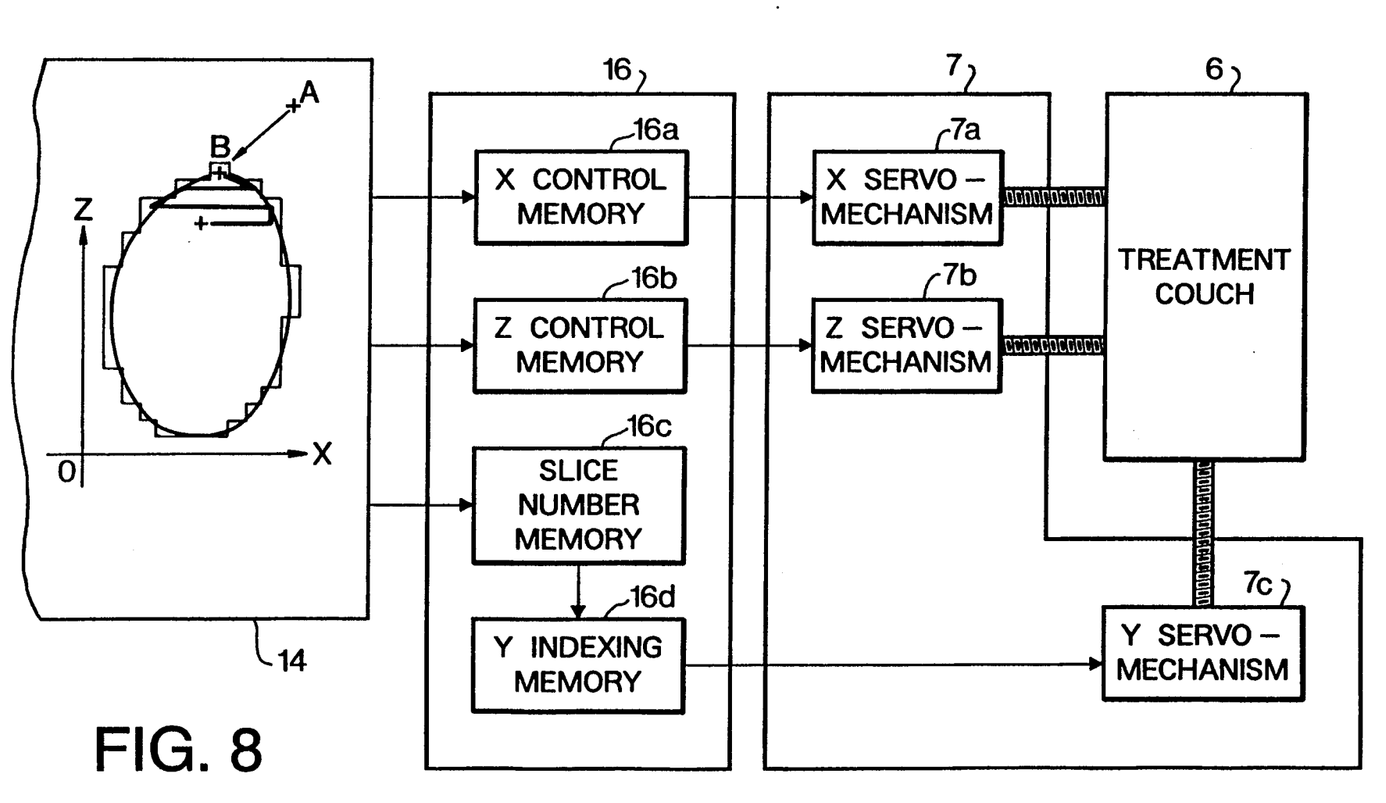
FIG. 8 is a schematic diagram showing a control system.

Referring to FIG. 8, the control system has a memory 16 for controlling the servomechanisms of the couch. The memory 16 comprises an X control memory 16a, a Z control memory 16b, a slice number memory 16c and a Y indexing memory 16d. The X control memory 16a is operatively connected to an X servomechanism 7a in the base 7 to feed the couch 6 in the X direction. Similarly, the Z control memory 16b is connected to a Z servomechanism 7b. The Y indexing memory 16d is connected to a Y servomechanism 7c to index the couch 6 in the Y direction by an increment $\Delta Y$.

In operation, the base 7 is clamped to the gantry 12 of the CT scanner, until the end of CT scanning. The longitudinal axis of the base 7 along with the Y direction of the couch 6 is perpendicular to the plane of CT image 14. At first, a scout view, like conventional radiography, is taken by feeding the couch in the Y direction. Then the position of the lesion is identified and the three coordinates $X_0$, $Y_0$ and $Z_0$ of an extreme end point $P_0$ of the lesion, which corresponds to the position B of a first slice, are decided and memorized in the memories 16a, 16b, 16c and 16d by inspecting the scout view along with precise information of CT or MR image and so on, which were obtained at another diagnosis division.

The CT slices are taken as usual by starting from the coordinate $Y_0$ and by moving the couch 6 in the Y direction with an interval $\Delta Y_0$. The magnitude of interval $\Delta Y_0$ is determined by taking the equivalent diameter of the radio-spot into consideration, and all $\Delta Y_0$ feeds are memorized in the Y indexing memory 16d together with other Y movements of the couch. After the CT scanning is finished, the Y coordinate of the couch is reset to the initial coordinate $Y_0$.

Figure 11:
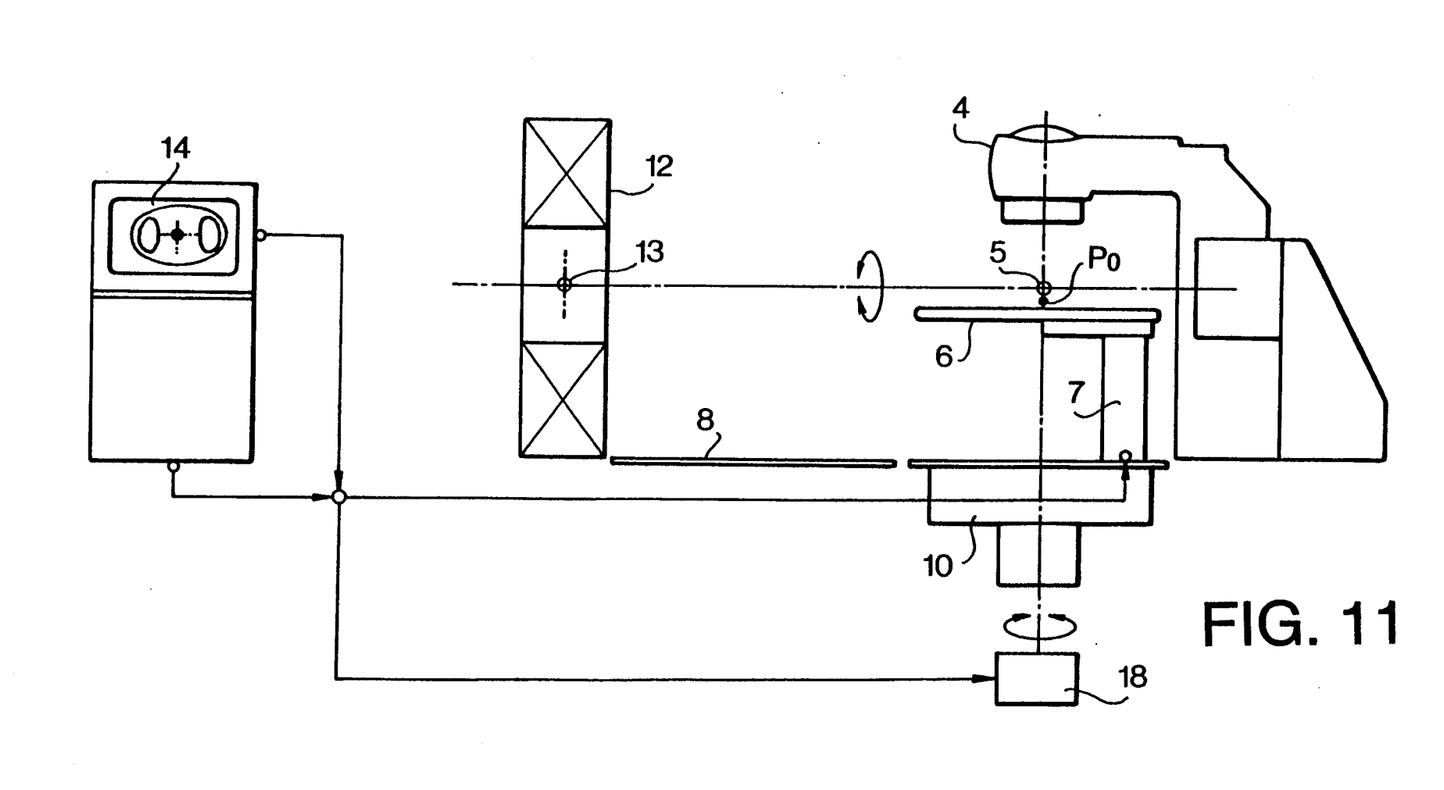
FIG. 11 is a side view of the system at the treatment.

Thereafter, the base 7 is unclamped from the gantry 12 and moved on the rail 8 to the position on the turntable 10 as shown in FIG. 11. The distance of this horizontal movement of the base 7 on the rail must be equal to that between the isocenter 5 and the center 13 of CT image plane. The latter distance is physically determined at the initial installation of the linear accelerator and the CT scanner.

Figure 9:
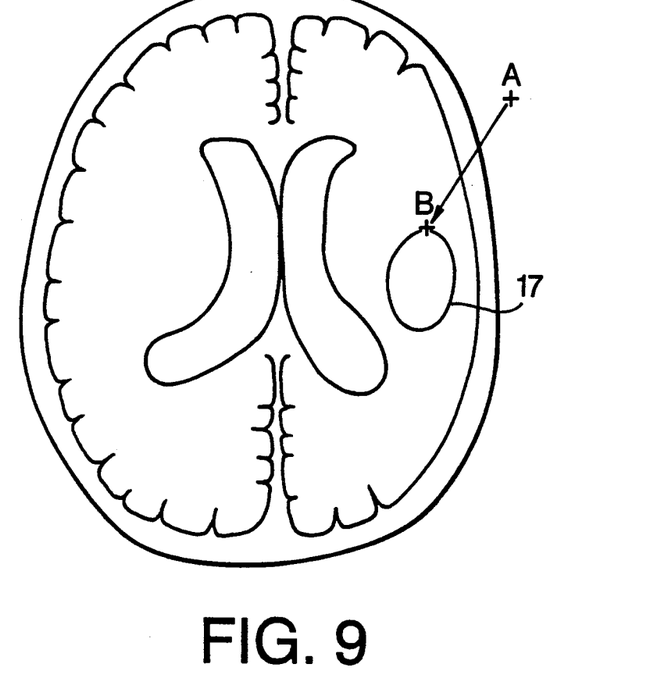
FIG. 9 illustrates a CT image on the CRT screen showing a brain tumor.

Referring to FIG. 9 showing one of the slices, the plus mark of the virtual isocenter is at the position A. Then the mark is shifted to the position B corresponding to an upper extreme point of the tumor by operating the light pen. Thereafter, a physician makes a decision of the region of interest to irradiate. The region is encircled with the light pen, so that a contour line 17 is imaged on the screen.

Figure 10:
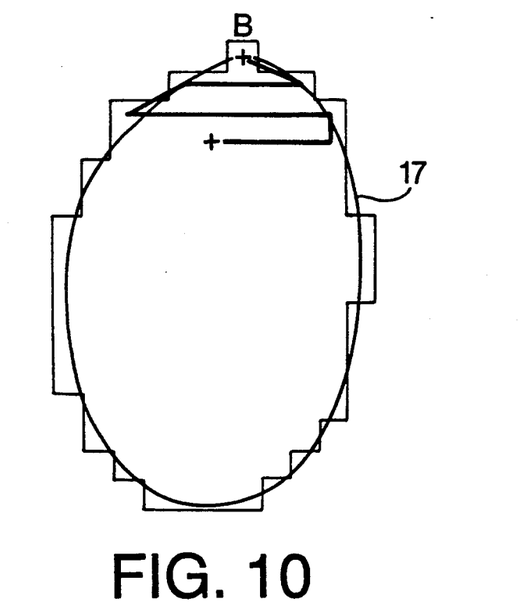
FIG. 10 is an enlarged view of the tumor in FIG. 9.

The screen is divided into a plurality of positions. Then, pushing a switch button initiates an automatic zigzag scanning motion of the mark within the encircled region on the X-Z plane as shown in FIGS. 8 and 10. The interval of the zigzag motion is determined by taking the equivalent diameter of the radio-spot into consideration. At the same time, the increments $\Delta X$ and $\Delta Z$ of all movements of the mark, such as the movement from A to B and the zigzag motion are stored in the X and Z memories 16a, 16b respectively. Namely, the coordinates of the positions on the contour line 17 are stored in the X, Z memories 16a, 16b and all positions in the contour are also stored in the memories. The memorizing operation is performed on all slices.

The treatment with the radio-spot is started from the point $P_0$. The actual point $P_0$ (FIG. 11) is automatically coincided with the isocenter 5 by controlling the X and Z servomechanisms 7a and 7b in accordance with the data stored in the memories 16a and 16b at the initial inspection of $P_0$. The Y axis control is started from $Y_0$ of the extreme end point $P_0$. The interval $\Delta Y_0$ at the treatment is determined to be equal to that in the CT scanning. On the other hand, the base 7 and the couch 6 are slowly rotated about the vertical axis in accordance with the turntable control with a controller 18 in FIG. 11 so as to make half revolution per treatment. The X-ray head 4 in FIG. 11 is continuously and reciprocatively rotated.

The X and Z servomechanisms 7a and 7b control the relative motion of the radio-spot in each slice. The radio-spot is actually fixed at the isocenter 5 of linear accelerator, therefore the couch 6 is moved in the X-Z plane relative to the base 7 so as to make the radio-spot cover the whole encircled region.

From the foregoing, it will be understood that the present invention provides a system which may exactly irradiate X-rays to an affected part and minimize the dose of X-rays to other parts than the lesion.

While the invention has been described in conjunction with preferred specific embodiment thereof, it will be understood that this description is intended to illustrate and not limit the scope of the invention, which is defined by the following claims.

What is claimed is:

1. A system for stereotactic radiotherapy comprising:

a first apparatus having a head for emanating an ionizing radiation, said head being rotatable about a horizontal axis, such that the ionizing radiation intersects said horizontal axis at an isocenter;

a second apparatus for taking a tomographic image, which is installed on the same floor as the first apparatus and which has a center for said tomographic image;

a turntable rotatable about a vertical axis passing through said isocenter;

driving means for reciprocatively rotating said head and for rotating said turntable;

a base mounted on said turntable being movable between said first and second apparatuses;

a treatment couch horizontally movably mounted on said base;

moving means for moving said couch with respect to said base along a longitudinal direction (Y) of said base and for moving said couch within a vertical (X-Z) plane perpendicular to said direction (Y);

positioning means for positioning said base in said second apparatus so that a positional relationship between said center and said base coincides with a positional relationship between said isocenter and the base when the base is moved from said second apparatus to said first apparatus;

storing means for storing data on a particular position in said tomographic image;

first control means for controlling said driving means for reciprocating said head and rotating said turntable; and second control means for controlling said moving means based on said stored data during the reciprocative rotation of said head and the rotation of the turntable so that said ionizing radiation is irradiated to a part in a patient on said couch dependent on said stored data of the position.

2. A system for stereotactic radiotherapy according to claim 1 wherein the first apparatus is a linear accelerator having an X-ray head.

3. A system for stereotactic radiotherapy according to claim 2 wherein the second apparatus is a CT scanner.

4. A system for stereotactic radiotherapy according to claim 1 wherein said moving means includes three servomechanisms for moving said couch in said longitudinal direction (Y) and within said vertical plane (X-Z).

5. A system for stereotactic radiotherapy according to claim 3 wherein said moving means is provided for intermittently moving said couch in said longitudinal direction at a regular interval for producing a plurality of CT slices.

6. A system for stereotactic radiotherapy according to claim 5 further including means for moving a mark on a CT image, and first storing means for storing a position of a trace of the movement of the mark, and second storing means for storing a position of said couch with respect to said base in said longitudinal direction at every CT slice, said control means being provided for moving said couch in said linear accelerator in accordance with the stored positions by said first and second storing means.

* * * * *